(12) United States Patent
Meudt et al.

(10) Patent No.: US 6,566,546 B2
(45) Date of Patent: May 20, 2003

(54) PROCESS FOR PREPARING 4-SUBSTITUTED 2-ALKYLBIPHENYLS AND 2-ALKOXYLBIPHENYLS

(75) Inventors: Andreas Meudt, Flörsheim-Weilbach (DE); Stefan Scherer, Büttelborn (DE); Frank Vollmüller, Frankfurt am Main (DE); Heinz Georg Kautz, Bierstein (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/073,568

(22) Filed: Feb. 11, 2002

(65) Prior Publication Data

US 2002/0115880 A1 Aug. 22, 2002

(30) Foreign Application Priority Data

Feb. 16, 2001 (DE) .......................... 101 07 227

(51) Int. Cl.⁷ .................. C07C 253/00; C07C 22/04
(52) U.S. Cl. ...................... 558/350; 570/182
(58) Field of Search ............ 558/350; 570/182

(56) References Cited

U.S. PATENT DOCUMENTS 5,254,776 A * 10/1993 Lang et al. ............ 570/190
5,416,235 A * 5/1995 Gilbert et al. ........... 558/350

OTHER PUBLICATIONS

Ernest H. Huntress, et al. "Fluorenones and Diphenic Acids. VI.1 Ring Cleavage of 2–Chloro, 2–Hydroxy–, 2–Amino–and 2–Sulfofluorenones with Potassium Hydroxide in Diphenyl Ether", Am. Chem. Soc., 1939, vol. 61, pp. 816 & 820.

de la Mare, et al., "The Kenetics and Mechanisms of Aromatic Halogen Substitution. Part XIV.1 Rates and Products of Chlorination of Methyl–substituted Biphenyls in Acetic Acid", J. Chem. Soc., 1962, pp. 3784–3796.

Nigel J. Brunce, et al., "Photolysis of Some ortho–Methylated Monochlorobiphenyls", J. Chem. Soc. Perkin Trans., 2, 1983, pp. 859–862.

* cited by examiner

Primary Examiner—Joseph K. McKane
Assistant Examiner—Kamala Saeed
(74) Attorney, Agent, or Firm—Scott E. Hanf

(57) ABSTRACT

A process for preparing 4-substituted 2-alkylbiphenyls and 2-alkoxybiphenyls of the formula (I),

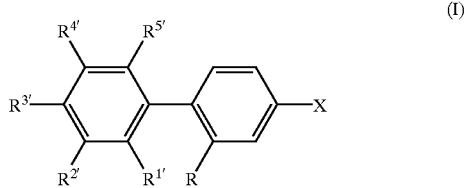

4 Claims, No Drawings

PROCESS FOR PREPARING 4-SUBSTITUTED 2-ALKYLBIPHENYLS AND 2-ALKOXYLBIPHENYLS

The invention relates to a process for preparing 4-substituted 2-alkybiphenyls and 2-alkoxybiphenyls.

Such 4-substituted biphenyls are versatile building blocks in organic synthesis and important intermediates in the synthesis of active compounds for the agrochemical and pharmaceutical industries.

Despite the existing high level of economic interest in these compounds, few preparative routes to compounds of this type having a specific substitution pattern have been described in the literature, and these routes are then, if they are available at all, expensive and complicated.

For example, no syntheses of the compounds 4-iodo-2-methylbiphenyl, 4-bromo-2-methylbiphenyl, 4-chloro-, 4-bromo- and 4-iodo-2-methoxybiphenyl have hitherto been documented in the chemical literature.

Various syntheses have been described for 4-chloro-2-methylbiphenyl, but these are all associated with serious disadvantages:

Thus, for example, irradiation of 3-chloro-2-methylbiphenyl, which is in itself difficult to prepare, in cyclohexane (J. Chem. Soc. Perkin Trans. 2, 1983, 859–862) gives the product as a mixture of isomers together with dehalogenation products.

Also known is the coupling of 4-chloro-1-iodo-2-methylbenzene and iodobenzene by means of copper at 270° C. (de la Mare, J. Chem. Soc. 1962, 3784–3796). The disadvantages are, in particular, the poor selectivities and thus low yields and the complicated preparation of the raw material chloroiodomethylbenzene, as well as the fact that the products obtained in this way have to be subjected to elaborate purification to meet the quality requirements for pharmaceutical applications.

A further known process is the diazotization of 4-amino-2-methylbiphenyl and heating with benzene (Huntress, J. Am. Chem. Soc. 1939, 816, 820). Here too, the preparation of the raw material aminomethylbiphenyl is very complicated; a further disadvantage is the use of carcinogenic benzene. In addition, the yields obtained are also unsatisfactory.

There is therefore a need for a process for preparing compounds of the formula (I) which starts out from commercially readily available and inexpensive starting compounds and makes it possible to obtain the target products in good yields and high purities.

The present invention achieves this object and provides a process for preparing 4-substituted 2-alkylbiphenyls and 2-alkoxybiphenyls of the formula (I),

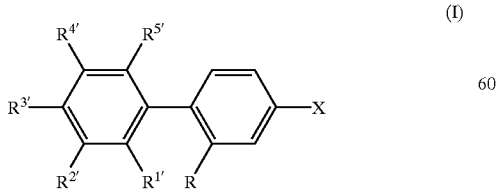

(I)

where the substituents X, R and $R^{1'}$ to $R^{5'}$ have the following meanings:

X is $NH_2$, NHAc, $NH(C=O)R^1$, where $R^1$=straight-chain or branched $C_1$–$C_8$-alkyl, in particular $C_1$–$C_4$-alkyl, fluorine, chlorine, bromine, iodine, $N_2H_3$ or cyanide, R is straight-chain or branched $C_1$–$C_8$-alkyl, in particular $C_1$–$C_4$-alkyl, or $C_1$–$C_5$-alkoxy, preferably $C_1$–$C_3$-alkoxy, and $R^{1'}$ to $R^{5'}$ are each, independently of one another, H, $CH_3$, straight-chain or branched $C_1$–$C_8$-alkyl, in particular $C_1$–$C_4$-alkyl, F, Cl, CN, $NO_2$, CHO, COOH, $CH_2OH$, $C(=O)CH_3$, $C_1$–$C_5$-alkoxy, in particular $C_1$–$C_3$-alkoxy, by reaction of phenylboronic acids of the formula (II) with 4-bromo- or 4-iodo-alkyl- or -alkoxy-anilines or -anilides of the formula (III) to form compounds of the formula (IV),

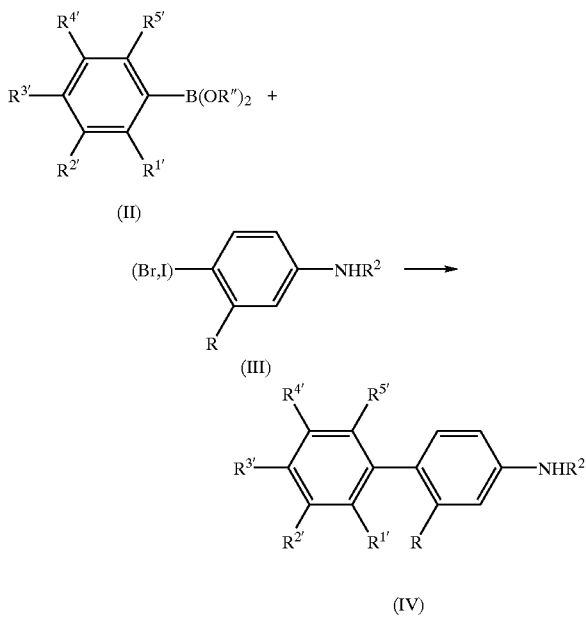

if desired, subsequent deacylation to form (V) and subsequent diazotization to form compounds of the formula (VI) and reaction with a nucleophile (X) or a reducing agent to give 4-substituted 2-alkylbiphenyls and 2-alkoxybiphenyls of the formula (I)

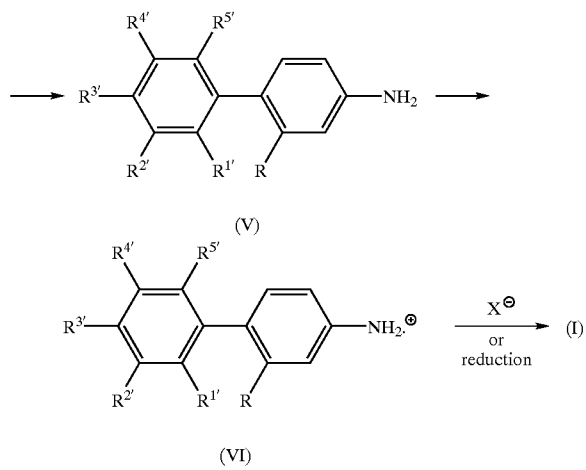

The process of the invention opens up an efficient, short route to the respective 4-substituted 2-alkylbiphenyl or 2-alkoxybiphenyl (I) which gives high yields in each step.

In the above formulae (III) and (IV), $R^2$ can be hydrogen, formyl or acyl having n=1 to 5 carbon atoms (C(=O)—$C_nH_{2n+1}$).

The arylboronic acids can be used as free boronic acids (R"=H), as boronic anhydrides or as esters of straight-chain or branched, monohydric or polyhydric alcohols (R"=$C_1$–$C_8$-alkyl, in particular $C_1$–$C_4$-alkyl-, or B(OR")$_2$ is a boronic anhydride radical). Preference is given to using the free boronic acids, the anhydrides or the esters with methanol, ethanol or glycol as starting compound.

The reason for the circuitous route via acylated anilines and subsequent deacylation is that, owing to the lability of the $NH_2$ group in coupling reactions, only moderate yields are observed in the coupling reaction in some cases. It has surprisingly been able to be shown that in these cases the abovementioned circuitous route is more economical despite the greater number of steps because of higher yields and product purities.

As stated above, X in the above formula can be $NH_2$, NHAc, NH(C=O)$R^1$ where $R^1$=straight-chain or branched $C_1$–$C_8$-alkyl, fluorine, chlorine, bromine, iodine, $N_2H_3$ or cyanide, and the corresponding reactants for preparing these compounds from the diazonium salt are then as described in the prior art, for example CuBr for X=Br, alkali metal iodides for X=I, CuCN for X=CN, or appropriate reducing agents such as sulfites or disulfites or $ZnCl_2$ for X=$N_2H_3$, to name only a few.

The aniline derivatives of the formula (V) are reacted by the Sandmeyer reaction via the corresponding diazo compounds of the formula (VI) with appropriate chloride, bromide, iodide or cyanide compounds to form 2-alkyl-or 2-alkoxy-4-chloro-, -bromo-, -iodo- or -cyano-biphenyls of the formula (I).

Hydrazino compounds of the formula (I) (X=$N_2H_3$) are preferably prepared by reacting the diazonium salts of the formula (VI) with a reducing agent, in particular a sulfite, hydrogensulfite, disulfite or tin chloride.

The raw materials for the synthesis of the invention are either commercially available or can be prepared simply and in good yields. 4-bromo- or 4-iodo-3-alkyl- or alkoxy-anilines or -anilides of the formula (III), for example, can all be procured commercially at an acceptable price, even in large amounts. The phenylboronic acids (II) to be used for the Suzuki couplings are likewise commercially available, but can in many cases be prepared more cheaply in good yields by reaction of the corresponding Grignard compounds with boron compounds using methods known to those skilled in the art.

The Suzuki couplings of boronic acids of the formula (II) with anilines of the formula (III) to form aminobiphenyls of the formula (IV) can be achieved by means of Pd-catalyzed coupling reactions which can be carried out by methods based on those of the prior art ("Metal-catalyzed Cross-coupling Reactions", Diederich/Stang, Wiley-VCH, Weinheim 1998). Suitable solvents for the coupling reaction are, for example, alcohols, DMSO, NMP, DMF, DMAc, ethers or hydrocarbons; preference is given to carrying out the coupling reaction in alcoholic solvents such as methanol, ethanol or glycol. The reaction is carried out in the presence of noble metal catalysts, in particular palladium-containing catalysts. In a preferred embodiment, use is made of palladium or nickel catalysts selected from the following group: $NiCl_2$, $PdCl_2$, $PdCl_2$(dppf), $PdCl_2$(PPh$_3$)$_2$, $PdCl_2$(dppe), $PdCl_2$(dppp), $PdCl_2$(dppb), $PdI_2$, $PdBr_2$ or Pd(OAc)$_2$, to name only a few (in these formulae, dppe=1,2-bis (diphenylphosphino)ethane, dppp=1,2-bis (diphenylphosphino)propane, dppb=1,2-bis (diphenylphosphino) butane and dppf=1,2-bis (diphenylphosphino)ferrocene, Ph=phenyl). In general, the catalyst is initially charged in the appropriate solvent and the boronic acid of the formula (II) and the aniline and anilide of the formula (III) are slowly added dropwise. During the addition, the temperature of the reaction solution is kept in the range from 0 to 150° C., in particular from 70 to 135° C. After addition of the reactants is complete, it may be useful to add a further 0.001–1 mol % of catalyst, based on the compound of the formula (II), to the reaction solution in order to achieve the highest possible conversion. The solution is subsequently refluxed for from 1 to 24 hours.

After the coupling is complete, the reaction mixture is worked up by, for example, pouring into water, extraction and evaporation, with the crude product being obtained as a solidified melt or a viscous oil. In some cases, the crude product precipitated on pouring into water can be recovered more simply by filtration.

The yields are generally from 85 to 98%, in particular from 90 to 95%.

The crude products obtained can easily be obtained in good yields and in highly pure form by recrystallization with addition of small amounts of activated carbon. However, in most cases it has been found to be possible to use the crude biphenyls of the formula IV without further purification.

When anilines with $R^2$=H are used, the anilines (V) ($R^2$=H) required for the diazotization are obtained directly; however, when anilides with $R^2$=formyl or acyl and having from 1 to 5 carbon atoms (C(=O)—$C_nH_{2n+1}$) (n=1–5) are used, an additional deacylation step is necessary. This can advantageously be carried out by boiling the crude anilide with the acid also used later in the diazotization step, e.g. hydrochloric, hydrobromide or sulfuric acid. This procedure offers a great advantage, since cleavage of the anilide results directly in a solution or suspension of the ammonium salt which can be diazotized directly and without prior setting free of the amino biphenyl (the carboxylic acids formed as coproduct in the cleavage do not interfere). Furthermore, the boiling of the anilides or amines formed with the acids, which is usually carried out for a number of hours, produces the product in a very fine form, so that the diazotizations proceed quantitatively in very short reaction times.

The further reactions of the diazonium salts formed to give the products of the formula (I) are carried out using methods based on those of the prior art, but these often have to be modified appropriately to adapt them to the frequently low solubilities of biphenyls. The reduction using customary reducing agents such as sulfite, hydrogensulfite or disulfite solutions or $SnCl_2$ leads to good yields of hydrazinobiphenyls, the Sandmeyer reaction with CuCN, CuBr or CuCl gives the corresponding compounds with X=CN, Br or Cl in yields of from 80 to 95%, and the reaction with iodide solutions leads to very good yields of 4-iodo-2-alkyl/alkoxybiphenyls.

The process of the invention is illustrated by the following examples, without the invention being restricted thereto:

EXAMPLE 1

Preparation of 2-methyl-4-acetaminobiphenyl 225 g of sodium carbonate and 0.15 g of $PdCl_2(PPh_3)_2$ in 450 ml of methanol are heated to reflux temperature. A solution of 342 g of 4-bromo-3-methylacetanilide and 270 g of the ethylene glycol ester of phenylboronic acid in 225 ml of methanol, which has been heated to 50° C., is added dropwise over a period of 60 minutes. During the addition, methanol is distilled off in such an amount that the internal temperature can be kept at at least 85° C. After addition is complete, a further 0.1 g of the Pd catalyst is added and the reaction mixture is refluxed for another 6 hours. After this time, the monitoring of the reaction by HPLC indicates a conversion of 99.9%. The remaining methanol is distilled off as completely as possible (620 ml), with the reaction mixture having to remain stirrable. 1250 ml of chlorobenzene are subsequently added. Hydrolysis is carried out by addition of 85 ml of water. At 70–80° C., the phases are separated and the aqueous phase is discarded. The organic phase is washed once with 50 ml of water and is subsequently filtered through a 0.5 cm thick layer of aluminum oxide. The chlorobenzene is distilled off at 300–500 mbar. The residue of crude 2-methyl-4-acetaminobiphenyl which remains is used further without further purification. The yield is quantitative.

The direct coupling of 4-bromo-3-methylaniline which was not acylated on the amino nitrogen proceeded in yields of only about 55%, and the remainder was converted by deamination into 2-methylbiphenyl, which was also not easy to separate from the desired reaction product.

EXAMPLE 2

Preparation of 2-methyl-4-aminobiphenyl hydrochloride 300 g of water and 296 g of HCl (37%) are added to the 2-methyl-4-acetaminobiphenyl prepared as described in Example 1. Any chlorobenzene still present is distilled off azeotropically, and the mixture is subsequently refluxed until HPLC monitoring indicates complete conversion (about 4 hours). The suspension obtained can be reacted further without further purification and without removal of the acetic acid formed as coproduct in the cleavage. The yield is (calculated from HPLC percentages by area) 99%.

EXAMPLE 3

Preparation of 4-iodo-2-methylbiphenyl

The reaction mixture from Example 2 is admixed with 300 ml of water and 100 ml of toluene and cooled to 0° C. 517.5 g of a 20% strength by weight solution of sodium nitrite in water are added dropwise at from 0 to 3° C. over a period of 2 hours. After stirring for another 15 minutes, a nitrite determination is carried out. If nitrite is no longer detectable, a further 2 g of nitrite solution are added, the mixture is stirred for another 15 minutes and nitrite is determined again. When the nitrite test is still positive after 15 minutes, conversion is complete and unreacted nitrite can be destroyed by addition of 0.5 g of aminosulfonic acid. At a temperature of 0–5° C., a total of 516 g of a 50% strength solution of Kl in water are added dropwise over a period of 30 minutes. To destroy residual unreacted diazonium salt, the mixture is heated at 60° C. for 15 minutes and subsequently cooled back down to 50° C. After addition of 750 ml of toluene, the phases are separated and the aqueous phase is extracted once more with 250 ml of toluene. The combined organic phases are deacidified and decolorized by stirring with 189 g of 2 M $Na_2CO_3$ solution in which 11 g of sodium disulfite have additionally been dissolved. Repeating the phase separation and filtering the dark solution gives 455 g of crude 4-iodo-2-methylbiphenyl as a toluene solution. Distilling off the toluene at 33 mbar/60° C. leaves crude 4-iodo-2-methylbiphenyl as a brownish, clear liquid which can be converted by distillation (although this is accompanied by partial thermal decomposition with losses in yield) into pure and colorless, very light-sensitive 4-iodo-2-methylbiphenyl (b.p. 140–150° C./2 mbar, yield of crude product=95%, after distillation 90%). The product has to be stored at 0–5° C. in the absence of light.

EXAMPLE 4

Preparation of 4-cyano-2-methylbiphenyl

The suspension of the diazonium salt prepared as described in Example 3 is reacted with a freshly prepared solution of CuCN in KCN solution according to methods described in the prior art (Organikum, 17th edition, VEB 1988). This gives 4-cyano-2-methylbiphenyl as a yellowish oil in a yield of 83%.

EXAMPLE 5

Preparation of 4-chloro-2-methylbiphenyl

The suspension of the diazonium salt prepared as described in Example 3 is reacted with a freshly prepared solution of CuCl in concentrated hydrochloric acid according to methods described in the prior art (Organikum, 17th edition, VEB 1988). This gives 4-chloro-2-methylbiphenyl as a yellowish solid in a yield of 86%.

EXAMPLE 6

Preparation of 4-bromo-2-methylbiphenyl

The suspension of the diazonium salt prepared as described in Example 3 is reacted with a freshly prepared solution of CuBr in concentrated hydrobromic acid according to methods described in the prior art (Organikum, 17th edition, VEB 1988). This gives 4-bromo-2-methylbiphenyl as a yellowish solid in a yield of 92%.

EXAMPLE 7

Preparation of 4-chloro-2-methylbiphenyl

The suspension of the diazonium salt prepared as described in Example 3 is reacted with a freshly prepared solution of CuCl in concentrated hydrochloric acid according to methods described in the prior art (Organikum, 17th edition, VEB 1988). This gives 4-chloro-2-methylbiphenyl as a slightly brownish oil in a yield of 84%.

EXAMPLE

Preparation of 4-hydrazino-2-methylbiphenyl

The suspension of the diazonium salt prepared as described in Example 3 is reacted with sodium sulfite solution according to methods described in the prior art (Organikum, 17$^{th}$ edition, VEB 1988). This gives 4-hydrazino-2-methylbiphenyl as a yellowish solid which decomposes very readily and therefore has to be stored at −20° C. or be immediately reacted further. The hydrochloride of the hydrazinobiphenyl can be kept for a few days at room temperature in the absence of air.

EXAMPLE 9

Preparation of 4-acetamino-2,4'-dimethylbiphenyl

The preparation of this compound was carried out by a method analogous to Example 1, but in this case the equivalent amount of the ethylene glycol ester of p-tolylboronic acid was used. Distilling off the chlorobenzene left the product as a viscous, light-brown oil in a yield of 95%; this can be purified further by crystallization from ethanol.

EXAMPLE 10

Preparation of 4-acetamino-2-methyl-4'-chlorobiphenyl

The preparation of this compound was carried out by a method analogous to Example 1, but in this case the equivalent amount of the ethylene glycol ester of p-chlorophenylboronic acid was used. Distilling off the chlorobenzene left the product as a light-brown solid.

What is claimed is:
1. A process for preparing 4-substituted 2-alkylbiphenyls and 2-alkoxybiphenyls of the formula (I),

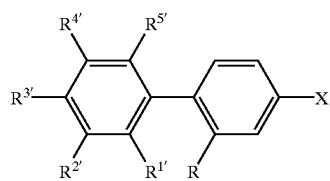

(I)

where the substituents X, R and R$^{1'}$ to R$^{5'}$ have the following meanings:

X is fluorine, chlorine, bromine, iodine, or a cyano group,
R is straight-chain or branched C$_1$–C$_8$-alkyl or C$_1$–C$_5$-alkoxy and
R$^{1'}$ to R$^{5'}$ are each, independently of one another, H, CH$_3$, straight-chain or branched C$_1$–C$_8$-alkyl, F, Cl, CN, NO$_2$, CHO, COOH, CH$_2$OH, C(=O)CH$_3$, C$_1$–C$_5$-alkoxy, comprising the steps of:
reacting phenylboronic acids of the formula (II) with 4-bromo- or 4-iodo-alkyl- or -alkoxy-anilines or -anilides of the formula (III) to form compounds of the formula (IV),

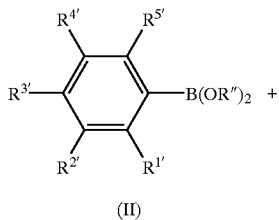

(II)

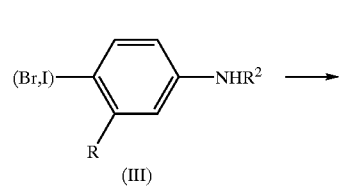

(III)

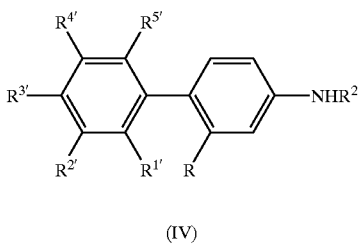

(IV)

where
R$^2$ is hydrogen, and
R" is H or C$_1$–C$_8$-alkyl or B(OR")$_2$ is a boronic anhydride radical; and reacting the compounds of formula (IV) with a nucleophile X, and optionally a Cu salt by the Sandmeyer reaction to give 4-substituted 2-alkylbiphenyls and 2-alkoxybiphenyls of the formula (I)

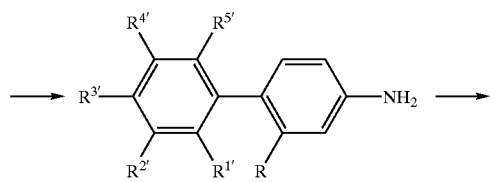

(V)

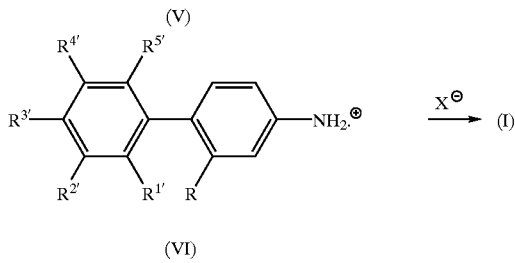

(VI)

or:
reacting phenylboronic acids of the formula (II) with 4-bromo- or 4-iodo-alkyl- or -alkoxy-anilines or -anilides of the formula (III) to form compounds of the formula (IV),

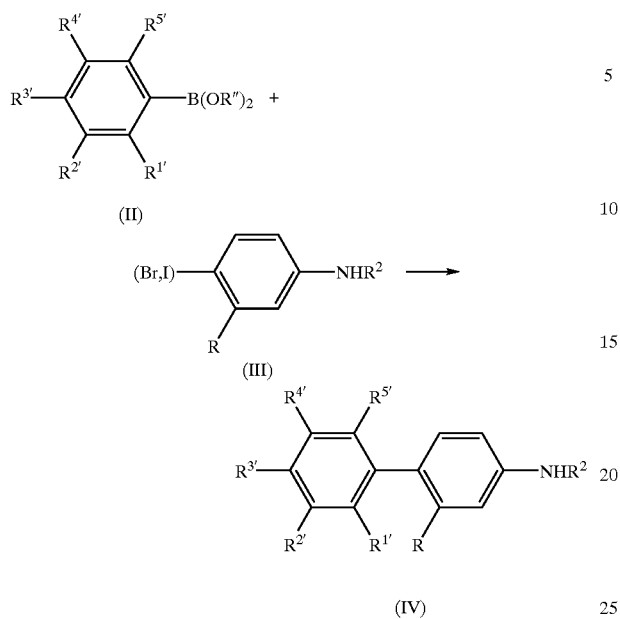

where
R² is formyl or acyl having from 1 to 5 carbon atoms (C(=O)—$C_nH_{2n+1}$) (n=1–5) and
R" is H or $C_1$–$C_8$-alkyl or B(OR")₂ is a boronic anhydride radical; deacylating the compounds of formula (IV) to form formula (V); diazotizating the compound of formula (V) to form compound of formula (VI); reacting formula (VI) with a nucleophile X, and optionally a Cu salt by a Sandmeyer reaction to give 4-substituted 2-alkylbiphenyls and 2-alkoxybiphenyls of the formula (I),

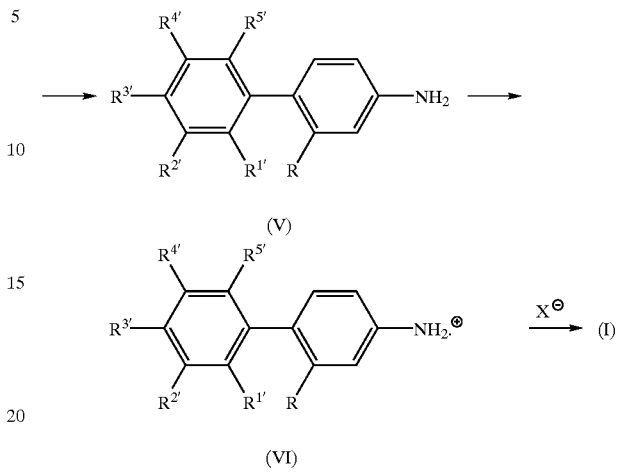

2. The process as claimed in claim 1, wherein the coupling reaction of the phenylboronic acids of the formula (II) with anilines or anilides of the formula (III) is carried out in an alcoholic solvent.

3. The process as claimed in claim 1, wherein the coupling reaction is carried out in the presence of a noble metal catalyst.

4. The process as claimed in claim 3, wherein a catalyst comprising nickel or palladium is used.

* * * * *